United States Patent [19]

Grasselli et al.

[11] 4,327,037
[45] Apr. 27, 1982

[54] PRODUCTION OF UNSATURATED NITRILES

[75] Inventors: Robert K. Grasselli, Chagrin Falls; Dev D. Suresh, Warrensville Heights; Harley F. Hardman, Lyndhurst, all of Ohio

[73] Assignee: The Standard Oil Company, Cleveland, Ohio

[21] Appl. No.: 881,313

[22] Filed: Feb. 27, 1978

Related U.S. Application Data

[62] Division of Ser. No. 430,964, Jan. 4, 1974, Pat. No. 4,139,552.

[51] Int. Cl.³ .......................................... C07C 120/14
[52] U.S. Cl. ................................................. 260/465.3
[58] Field of Search ....................................... 260/465.3

[56] References Cited

U.S. PATENT DOCUMENTS

| 3,642,930 | 2/1972 | Grasselli et al. | 260/465.3 X |
| 3,849,337 | 11/1974 | Manara et al. | 260/465.3 X |
| 3,883,573 | 5/1975 | Milberger et al. | 260/465.3 |
| 3,892,794 | 7/1975 | Grasselli et al. | 260/465.3 |
| 3,911,089 | 10/1975 | Shiraishi et al. | 260/465.3 X |

Primary Examiner—Joseph Paul Brust
Attorney, Agent, or Firm—John E. Miller, Jr.; Herbert D. Knudsen; Larry W. Evans

[57] ABSTRACT

Catalysts containing iron, molybdenum, bismuth and nickel, cobalt, magnesium, zinc, cadmium, calcium or beryllium have been found to give especially large volumes of acrylonitrile or methacrylonitrile in a given time when manganese, antimony, thorium, zirconium, yttrium or mixtures thereof are incorporated into the catalyst.

1 Claim, No Drawings

PRODUCTION OF UNSATURATED NITRILES

This is a division of application Ser. No. 430,964 filed Jan. 4, 1974, now U.S. Pat. No. 4,139,552, issued Feb. 13, 1979.

BACKGROUND OF THE INVENTION

A number of very desirable ammoxidation catalysts are known which represent the base catalysts to which the elements of the invention are added. These catalysts are used to produce acrylonitrile or methacrylonitrile under certain conditions with high per pass conversions. Under these conditions, if the amount of olefin fed over the catalyst in a given time is increased significantly, the per pass conversion tends to drop. In some instances, the per pass conversion to unsaturated nitriles drops markedly. Since the viability of a commercial operation is significantly affected by the amount of product that can be prepared in a given time, the present invention is directed at the problem in the art of increasing the production of product in a given time while maintaining high per pass conversions.

SUMMARY OF THE INVENTION

It has now been discovered in the process for the ammoxidation of propylene or isobutylene by contacting propylene, isobutylene or mixtures thereof with molecular oxygen and ammonia in the vapor phase in the presence of a catalyst, the improvement comprising using as the catalyst a catalyst wherein the ratio of the elements is described by the empirical formula $$A_a C_b D_d Fe_e Bi_e Mo_{12} O_x$$

wherein
  A is manganese, antimony, thorium zirconium, yttrium or mixture thereof;
  C is an alkali metal, thallium, indium, silver, copper, a rare earth metal, boron, phosphorus, arsenic or mixture thereof; and
  D is nickel, cobalt, magnesium, cadmium, calcium, zinc, beryllium or mixture thereof; and
wherein
  a is greater than zero to about 4;
  b is 0 to 4;
  c is 0.1 to about 20;
  d and e are independently about 0.1 to about 10; and
  x is the number of oxygens required to satisfy the valence requirements of the other elements present.

The process of the present invention provides a commercially feasible process for preparing large quantities of acrylonitrile or methacrylonitrile in a given period of time at high per pass conversions.

The amount of acrylonitrile or methacrylonitrile produced in an ammoxidation reaction is essentially a function of (1) the amount of olefin fed to the reactor in a given period of time, and (2) the single pass yield to the product. As noted above, catalysts useful in ammoxidation reactions have been limited to a certain range of feed rates to provide high per pass conversions. When higher feed rates are attempted, the single pass yield drops and the reaction becomes inefficient. At very high per pass conversions, the feed rate is so slow that the production rate suffers. The present invention solves this problem by the discovery of catalysts that can accept a high reactant feed rate while at the same time maintain a high single pass yield.

The reactant feed rate is normally stated as "WWH" and is measured according to the following formula:

$$WWH = \frac{\text{weight of olefin fed}}{\text{weight of catalyst} \times \text{hours}}$$

It can be seen from the formula that the rate of reactant feed varies directly with the WWH—as the WWH increases, the rate of reactant feed increases.

The second variable is the single pass yield. Single pass yield is stated in terms of mole percent according to the following formula for acrylonitrile.

$$\text{single pass yield, mole \%} = \frac{\text{moles of acrylonitrile in reactor effluent}}{\text{moles of propylene fed}} \times 100$$

It is seen that the amount of product formed is a direct function of the per pass conversion.

The central aspect of the present invention is the catalyst employed. The catalyst is suitably any catalyst containing the elements described in the formula above. Broadly, the base catalysts contain at least iron and molybdenum and bismuth plus at least one of nickel, cobalt, magnesium, cadmium, calcium or beryllium. In addition to these base elements, there is a large number of optional elements that could be incorporated into the catalyst. The base catalysts on which the invention is built are known catalysts useful for ammoxidation reactions. Accordingly, the base catalyst and its preparations are not the subject of the present invention even though there are preferred variations in the base catalyst.

The present invention is the incorporation of manganese, antimony, thorium, zirconium, yttrium or mixture thereof into the base catalyst to provide higher rates of production at high per pass conversions.

The elements added by the invention can be incorporated into the catalyst by any of the techniques that are employed to produce the base catalyst. A preferred method is coprecipitating a soluble compound of the element in the formation of the catalytic matrix. A preferred method of accomplishing these preparations are shown in the Specific Embodiments.

The manganese, antimony, thorium, zirconium or yttrium can be incorporated into the catalysts in any amount that is effective to obtain improved results of the present invention. Although this range may vary, a preferred range is 0.01 to about 4, and a more preferred range is about 0.1 to about 3.

Although a mixture of all the added elements of the invention could be used, it is preferred to use each of these elements separately in the catalyst. In the catalyst formula, this is accomplished by separately setting A equal each of these elements.

The base catalyst to which the elements of the invention are added also has preferred embodiments. Preferred are catalysts that contain nickel or cobalt or mixtures thereof, i.e. wherein D is nickel, cobalt or mixtures thereof.

The catalysts of the invention are suitably used in supported or unsupported form. Representative examples of carrier materials include silica, alumina, zirconia, titania, boron phosphate and the like.

The reactants, process conditions and other reaction parameters of the reaction are known in the art of the ammoxidation of propylene and isobutylene. The conditions, reactors and the like are not substantially changed from the art. The temperature may range from about 200° to about 600° C. with about 300° to about 500° C. being preferred. The reaction may be conducted in a fluid- or a fixed-bed reactor using atmospheric, subatmospheric or superatmospheric pressure. A feasible commercial application could be use of the present invention in a fluidized-bed reactor at superatmospheric pressure.

Since the present invention is primarily designed to feed more olefin over a catalyst in a given time, it is understood that the feed rates and composition of the feed could be altered from the art. Expressed in terms of WWH, the feed of olefin over the catalyst is preferably between about 0.05 and about 0.25.

Using the present invention, large quantities of acrylonitrile or methacrylonitrile are produced at high olefin feed rates and high per pass conversions.

COMPARATIVE EXAMPLE A AND EXAMPLES 1-6

Ammoxidation of Propylene.

Various catalysts of the invention were prepared as follows:

COMPARATIVE EXAMPLE A

80% $P_{0.5}K_{0.1}Ni_{2.5}Co_{4.5}Fe_3BiMo_{12}O_x$ and 20% $SiO_2$

An aqueous slurry was prepared containing 127.12 g. of $(NH_4)_6Mo_7O_{24}.4H_2O$, 102.74 g. of Nalco 40% silica sol and 6.92 g. of a 42.5% solution of $H_3PO_4$. Separately, a solution of 72.72 g. $Fe(NO_3)_3.9H_2O$, 29.11 g. of $Bi(NO_3).5H_2O$, 78.58 g. of $Co(NO_3)_2.6H_2O$, 43.62 g. of $Ni(NO_3)_2.6H_2O$ and 6.07 g. of a 10% solution of $KNO_3$ was prepared. The solution was added to the slurry, and the mixture was evaporated to a paste. The paste was dried at 110° C. over night, and then heat treated at 290° C. for three hours, 425° C. for three hours and 550° C. for 16 hours.

EXAMPLE 1

80% $Mn_{0.5}K_{0.1}Ni_{2.5}Co_{4.5}Fe_3BiMo_{12}O_x$ and 20% $SiO_2$

The same procedure was used, except that 10.74 g. of a 50 wt. % solution of $Mn(NO_3)_2$ was used instead of the phosphorus.

EXAMPLE 2

80% $Sb_{0.5}K_{0.1}Ni_{2.5}Co_{4.5}Fe_3BiMo_{12}O_x$ and 20% $SiO_2$

The same procedure except that 4.38 g. of $Sb_2O_3$ was used instead of the phosphorus.

EXAMPLE 3

80% $Sb_{0.5}K_{0.2}Ni_{2.5}Co_{4.5}Fe_3BiMo_{12}O_x$ and 20% $SiO_2$

The same procedure as Example 2 was used except that twice the amount of potassium nitrate was used.

EXAMPLE 4

80% $Th_{0.5}K_{0.1}Ni_{2.5}Co_{4.5}Fe_3BiMo_{12}O_x$ and 20% $SiO_2$

The same procedure was used as above except that 16.56 g. of $Th(NO_3)_4.4H_2O$ was used instead of the phosphorus.

EXAMPLE 5

80% $Zn_{0.5}K_{0.1}Ni_{2.5}Co_{4.5}Fe_3BiMo_{12}O_x$ and 20% $SiO_2$

The same procedure was used except that 9.68 g. of $ZrOCl_2.8H_2O$ was used instead of the phosphorus.

EXAMPLE 6

80% $Y_{0.5}K_{0.1}Ni_{2.5}Co_{4.5}Fe_3BiMo_{12}O_x$ and 20% $SiO_2$

The same procedure was used except that 10.96 g. of $Y(NO_3)_3.5H_2O$ was used instead of the phosphorus.

The catalysts were ground and screened to give 20 to 35 mesh fraction that was charged to a 5 cc. reaction zone of a tubular reactor constructed of stainless steel. The ammoxidation was carried out using a feed of propylene/ammonia/oxygen/nitrogen/steam of 1.8/2.2/3.6/2.4/6. The temperature of the bath surrounding the reactor was maintained at 420° C., and the apparent contact time was three seconds.

The results of these experiments are given in Table I. The results are expressed as follows:

$$\% \text{ conversion} = \frac{\text{moles of propylene reacted} \times 100}{\text{moles of propylene charged}}$$

$$\% \text{ selectivity} = \frac{\text{moles of acrylonitrile produced} \times 100}{\text{moles of propylene reacted}}$$

$$\% \text{ single pass yield} = \frac{\text{moles of acrylonitrile formed} \times 100}{\text{moles of propylene charged}}$$

TABLE I

Ammoxidation of Propylene Using $A_{0.5}K_{0.1}Ni_{2.5}Co_{4.5}Fe_3BiMo_{12}O_x$

| | | Results, % | | |
|---|---|---|---|---|
| Example | Catalyst, A = | Conv. | Select. | Single Pass Yield |
| Comp. A | P | 92.0 | 79 | 73.1 |
| 1 | Mn | 99.6 | 82 | 81.8 |
| 2 | Sb | 100 | 76 | 75.9 |
| 3 | Sb* | 100 | 77 | 77.2 |
| 4 | Th | 94.2 | 83 | 78.2 |
| 5 | Zr | 98.8 | 77 | 76.3 |
| 6 | Y | 99.6 | 74 | 73.9 |

*$K_{0.2}$ instead of $K_{0.1}$

COMPARATIVE EXAMPLE B AND EXAMPLES 7-10

Cesium-containing catalysts.

In the same manner as described above, catalysts of the invention containing cesium were prepared. The catalysts were prepared as shown above except that 1.18 g. of $CsNO_3$ was added instead of the potassium nitrate. In the same manner as shown above, the catalysts were tested in the ammoxidation of propylene. The results of these experiments are given in Table II.

TABLE II

Ammoxidation of Propylene Using $A_{0.5}Cs_{0.1}Ni_{2.5}Co_{4.5}Fe_3BiMo_{12}O_x$

| | | | Results, % | | |
|---|---|---|---|---|---|
| Example | Catalyst, A = | Temp., °C. | Conv. | Select. | Single Pass Yield |
| Comp. B | P | 420 | 86.8 | 72 | 62.2 |
| 7 | Mn | " | 74.3 | 81 | 60.5 |
| 8 | " | 440 | 86.1 | 82 | 70.2 |
| 9 | Sb | 420 | 97.7 | 81 | 79.0 |
| 10 | " | 440 | 99.5 | 78 | 78.0 |

EXAMPLES 11-17

Ammoxidation of isobutylene.

In the manner described above, various catalysts were prepared and tested in the ammoxidation of isobutylene to methacrylonitrile. The reactions were run at 400° C. using a feed of isobutylene/ammonia/air/steam of 1/1.5/11/4. The apparent contact time was three seconds, except in Example 16 where the contact time was six seconds. The catalyst of Example 14 received, in addition to the heat treatment described above, a treatment at 600° C. for three hours. All catalysts contained 20% $SiO_2$. The results are given in Table III based on methacrylonitrile.

TABLE III

Ammoxidation of Isobutylene With $A_aNi_{2.5}Co_{4.5}Fe_3BiMo_{12}O_x$

| Example | Catalyst, $A_a =$ | Results, % | | |
|---|---|---|---|---|
| | | Conv. | Select. | Single Pass Yield |
| 11 | $Sb_{0.5}K_{0.2}$ | 100 | 69 | 69.0 |
| 12 | $Mn_{0.5}Cs_{0.1}$ | 99.8 | 75 | 74.9 |
| 13 | $Sb_{0.5}Cs_{0.1}$ | 100 | 76 | 75.8 |
| 14 | $Sb_{0.5}Cs_{0.2}$ | 99.9 | 79 | 79.4 |
| 15 | $Sb_{0.5}Cs_{0.2}$* | 100 | 82 | 81.6 |
| 16 | $Sb_{0.5}Cs_{0.5}$ | 99.9 | 79 | 79.4 |
| 17 | $Sb_{0.5}Cs_{0.5}$** | 100 | 82 | 81.8 |

*additional heat treatment for three hours at 600° C.
**contact time 6 seconds

In the same manner as shown above, other catalysts of the invention, for example, those without an alkali metal or those with thallium, are employed in ammoxidation reactions.

We claim:

1. In the process for the ammoxidation of propylene or isobutylene by contacting propylene, isobutylene or mixtures thereof with molecular oxygen and ammonia in the vapor phase in the presence of a catalyst, the improvement comprising using as the catalyst $Sb_{0.5}Cs_{0.5}Ni_{2.5}Co_{4.5}Fe_3BiMo_{12}O_x$ wherein x is the number of oxygens required to satisfy the valence requirements of the other elements present.

* * * * *